US008328850B2

(12) United States Patent
Bernard et al.

(10) Patent No.: US 8,328,850 B2
(45) Date of Patent: Dec. 11, 2012

(54) DEVICE FOR IMMOBILIZING A CONNECTING ROD IN AN OSSEOUS ANCHORING ELEMENT OF A RACHIDIAN IMPLANT

(75) Inventors: Pierre Bernard, Bordeaux (FR); Tiphaine Leport, Lille (FR); Jean-Yves Leroy, Campagne les Hesdin (FR); Pascal Rokegem, Saint-Laurent Blangy (FR); Guy Viart, Saint-Leger (FR); Arnaud Pommier, Raimbeaucourt (FR)

(73) Assignee: Choice Spine, LP, Knoxville, TN (US)

( * ) Notice: Subject to any disclaimer, the term of this patent is extended or adjusted under 35 U.S.C. 154(b) by 1518 days.

(21) Appl. No.: 10/682,541

(22) Filed: Oct. 10, 2003

(65) Prior Publication Data
US 2005/0027292 A1 Feb. 3, 2005

(30) Foreign Application Priority Data

Dec. 23, 2002 (FR) .................... 02 16441
Jul. 17, 2003 (FR) .................... 03 08701

(51) Int. Cl.
*A61B 17/70* (2006.01)
(52) U.S. Cl. .................................... 606/264
(58) Field of Classification Search .......... 606/61, 606/66, 72–73, 264, 265, 267, 270, 272, 606/273, 275, 278, 305, 308, 319, 328; 403/326, 403/337, 362; 411/431, 501
See application file for complete search history.

(56) References Cited

U.S. PATENT DOCUMENTS

| 5,346,493 | A | * | 9/1994 | Stahurski et al. | 606/61 |
|---|---|---|---|---|---|
| 6,077,262 | A | * | 6/2000 | Schlapfer et al. | 606/61 |
| 6,090,111 | A | * | 7/2000 | Nichols | 606/61 |
| 6,110,172 | A | * | 8/2000 | Jackson | 606/61 |
| 6,302,888 | B1 | * | 10/2001 | Mellinger et al. | 606/73 |
| 6,540,749 | B2 | * | 4/2003 | Schafer et al. | 606/61 |
| 6,565,565 | B1 | * | 5/2003 | Yuan et al. | 606/61 |
| 6,585,737 | B1 | * | 7/2003 | Baccelli et al. | 606/61 |
| 6,740,086 | B2 | * | 5/2004 | Richelsoph | 606/60 |
| 6,755,829 | B1 | * | 6/2004 | Bono et al. | 606/61 |
| 6,786,903 | B2 | * | 9/2004 | Lin | 606/23 |
| 6,896,877 | B2 | * | 5/2005 | Calello et al. | 424/70.1 |
| 2004/0097933 | A1 | * | 5/2004 | Lourdel et al. | 606/61 |
| 2005/0033296 | A1 | * | 2/2005 | Bono et al. | 606/61 |

FOREIGN PATENT DOCUMENTS

| DE | 199 51 145 A1 | 5/2001 |
|---|---|---|
| EP | 1 064 885 A1 | 1/2001 |
| EP | 1 190 678 A2 | 3/2002 |
| FR | 2 697 992 | 5/1994 |
| FR | 2 729 291 | 7/1996 |
| FR | 2 795 623 | 1/2001 |

* cited by examiner

*Primary Examiner* — Alvin Stewart
*Assistant Examiner* — David Comstock
(74) *Attorney, Agent, or Firm* — Luedeka Neely Group, PC

(57) ABSTRACT

The immobilization device for a connecting rod (2) in an osseous anchoring element (3) of a rachidian implant (4) comprises an osseous anchoring implant (3) comprising retaining means (14, 15) adapted to deform elastically under a pressure force F and a blocking element (5) comprising on the one hand lugs (33, 34) which coact with the retaining means (14, 15) to permit the securement of the blocking element (5) on the osseous anchoring element (3), and on the other hand, a tightening screw (31) permitting immobilizing in rotation and in translation the connecting rod (2) between the osseous anchoring element (3) and the blocking element (5).

20 Claims, 18 Drawing Sheets

DEVICE FOR IMMOBILIZING A CONNECTING ROD IN AN OSSEOUS ANCHORING ELEMENT OF A RACHIDIAN IMPLANT

BACKGROUND OF THE INVENTION

The present invention relates to a device for immobilizing a connecting rod in an osseous anchoring element of a rachidian implant.

There are known different types of immobilization devices which, because of their particular structure, permit blocking in rotation and in translation the connecting rod in an osseous anchoring element of a rachidian implant.

SUMMARY OF THE INVENTION

The immobilization device according to the present invention has for its object to improve the retention of the blocking element on the osseous anchoring element, whilst preserving the independent securements for retaining on the one hand the connecting rod and on the other hand the blocking element.

The immobilization device according to the present invention comprises an osseous anchoring element comprising retaining means adapted to deform elastically under the pressure of a force F and a blocking element comprising on the one hand lugs which coact with the retaining means to promote the securement of the blocking element on the osseous anchoring element and on the other hand a tightening screw permitting the immobilization in rotation and in translation of the connecting rod between the osseous anchoring element and the blocking element.

The immobilization device according to the present invention comprises:

an osseous anchoring element provided with a head comprising two vertical walls delimiting a central opening of U shape whose bottom has a part cylindrical profile, each vertical wall being constituted by a central surface bordered laterally and on each side by elastic blades separated respectively from said central surface by vertical slots, said elastic blades comprising respectively in their upper portion a snap-in tooth, and a blocking element comprising a seat with a part cylindrical profile, a screw-threaded bore opening within the seat, a tightening screw coacting with the screw-threaded bore and lugs which coact respectively with a tooth secured to elastic blades.

The immobilization device according to the present invention comprises an osseous anchoring element whose central surface of each vertical wall is pierced with a hole opening within the central opening of U shape.

The immobilization device according to the present invention comprises an osseous anchoring element whose elastic blades of the head comprise respectively in their upper portion a tooth whose external profile is convexly rounded and inclined.

The immobilization device according to the present invention comprises a blocking element whose lower surface comprises, in a direction parallel to the axis XX' of the connecting rod, a seat having a part cylindrical profile.

The immobilization device according to the present invention comprises a blocking element whose upper surface, opposite the lower one, comprises at its middle a screw-threaded bore opening within the seat and in which coacts a tightening screw.

The immobilization device according to the present invention comprises a blocking element which has a first pair of opposite lateral surfaces comprising respectively above the seat an impression adapted to coact with an instrument for the manipulation and the emplacement of said blocking element on the osseous anchoring element.

The immobilization device according to the present invention comprises a blocking element which has a second pair of opposite lateral surfaces which are each secured to two lugs disposed in the width of said blocking element and positioned in prolongation of the first pair of lateral surfaces.

The immobilization device according to the present invention comprises a blocking element of which each lug comprises respectively in its upper portion an inclined or beveled flat whose lower base is positioned in the plane containing each of said first pairs of lateral surfaces.

The immobilization device according to the present invention comprises a blocking element of which each lug comprises respectively in its lower portion and opposite inclined flats, a rounded profile.

The immobilization device according to the present invention comprises a blocking element in which the distance d separating two lugs is less than that provided between two teeth of a same vertical wall of the osseous anchoring element.

The immobilization device according to the present invention comprises elastic blades which deform, under a pressure of a force F applied to the blocking element, laterally in the direction of the central surface of each wall of the osseous anchoring element.

The immobilization device according to the present invention comprises:

an osseous anchoring element provided with a head comprising two vertical truncated walls delimiting a central opening of U shape whose bottom has a part cylindrical profile, each vertical wall being constituted by a central surface bordered laterally and on each side by elastic blades separated respectively from said central surface by vertical slots, said elastic blades comprising respectively in their upper portion a snap-in tooth, and a blocking element comprising a seat with a part cylindrical profile, a screw-threaded bore opening within the seat, a tightening screw coacting with the screw-threaded bore and lugs which coact respectively with a tooth secured to the elastic blades.

The immobilization device according to the present invention comprises a head having two vertical walls with truncated profile disposed one facing the other and in parallel planes so as to delimit a first central opening of U shape carried by the axis XX' of the connecting rod and whose bottom has a part cylindrical profile, and a second opening perpendicular to the axis XX' and to the first opening.

The immobilization device according to the present invention comprises a head having two perpendicular openings which permit delimiting at each corner of the head elastic blades adapted to deform elastically under the pressure of a force F.

The immobilization device according to the present invention comprises a head provided with elastic blades comprising respectively in their upper portion a tooth whose hooking profile is turned in the inward direction of the second opening and above the central surface of each vertical wall.

The immobilization device according to the present invention comprises a head of which each tooth comprises, above its hooking portion and in the opening direction, an inclined external profile prolonged in the exterior direction by a convexly curved profile.

The immobilization device according to the present invention comprises a blocking element having a lower surface comprising in a direction parallel to the axis XX', a seat having a part cylindrical profile so as to coact with the connecting rod, an upper surface comprising at its middle a screw-threaded bore opening within the seat and in which coacts a tightening screw, and lateral surfaces parallel two by two and of which at least two are secured respectively to two lugs in the form of a tooth.

The immobilization device according to the present invention comprises a blocking element of which each lug comprises a hooking portion positioned retracted from and at a certain distance d1 from the lateral and opposed surfaces of the blocking element.

The immobilization device according to the present invention comprises:
- an osseous anchoring element provided with a head comprising two vertical walls delimiting a central opening of U shape whose bottom has a part cylindrical profile, each vertical wall being separated from the bottom of the central opening by a vertical slot giving a certain elasticity to each wall in a direction YY', said vertical walls comprising respectively at each end a profile in the form of an elastic hooking blade disposed one facing the other and on opposite sides of the central opening, said elastic blades comprising respectively in their upper portion a snap-in tooth,
- and a blocking element comprising a seat with a part cylindrical profile, a screw-threaded bore opening within the seat, a tightening screw coacting with the screw-threaded bore, and lugs which coact respectively with a tooth secured to the elastic blades.

The immobilization device according to the present invention comprises a head of which each vertical wall comprises on its internal surface and between the hooking blades, a vertical seat.

The immobilization device according to the present invention comprises a head whose elastic blades comprise respectively in their upper portion a tooth whose hooking profile is turned in the direction of the interior of the central opening.

The immobilization device according to the present invention comprises a head of which each tooth comprises above its hooking portion and in the direction of opening, an external inclined profile prolonged in the direction of the outside by a convexly curved profile.

The immobilization device according to the present invention comprises a blocking element comprising an internal surface comprises in a direction parallel to the axis XX', a seat having a part cylindrical profile so as to coact with the connection rod, an upper surface comprising at its middle a screw-threaded bore opening within the seat and in which coacts a tightening screw, and lateral surfaces parallel two by two and of which at least two are secured respectively to two lugs in the form of teeth.

The immobilization device according to the present invention comprises a blocking element of which each lateral surface disposed in a plane parallel to the axis XX' of the seat comprises two lugs in the form of a tooth separated by a vertical rib having a vertical central seat.

The immobilization device according to the present invention comprises a blocking element of which the hooking portions of the lugs are closed opposite lateral surfaces by means of the corresponding vertical rib.

The description which follows with respect to the accompanying drawings, given by way of non-limiting examples, will permit better comprehension of the invention, the characteristics which it has, and the advantages which it is adapted to provide:

DETAILED DESCRIPTION OF THE INVENTION

Figure 1:
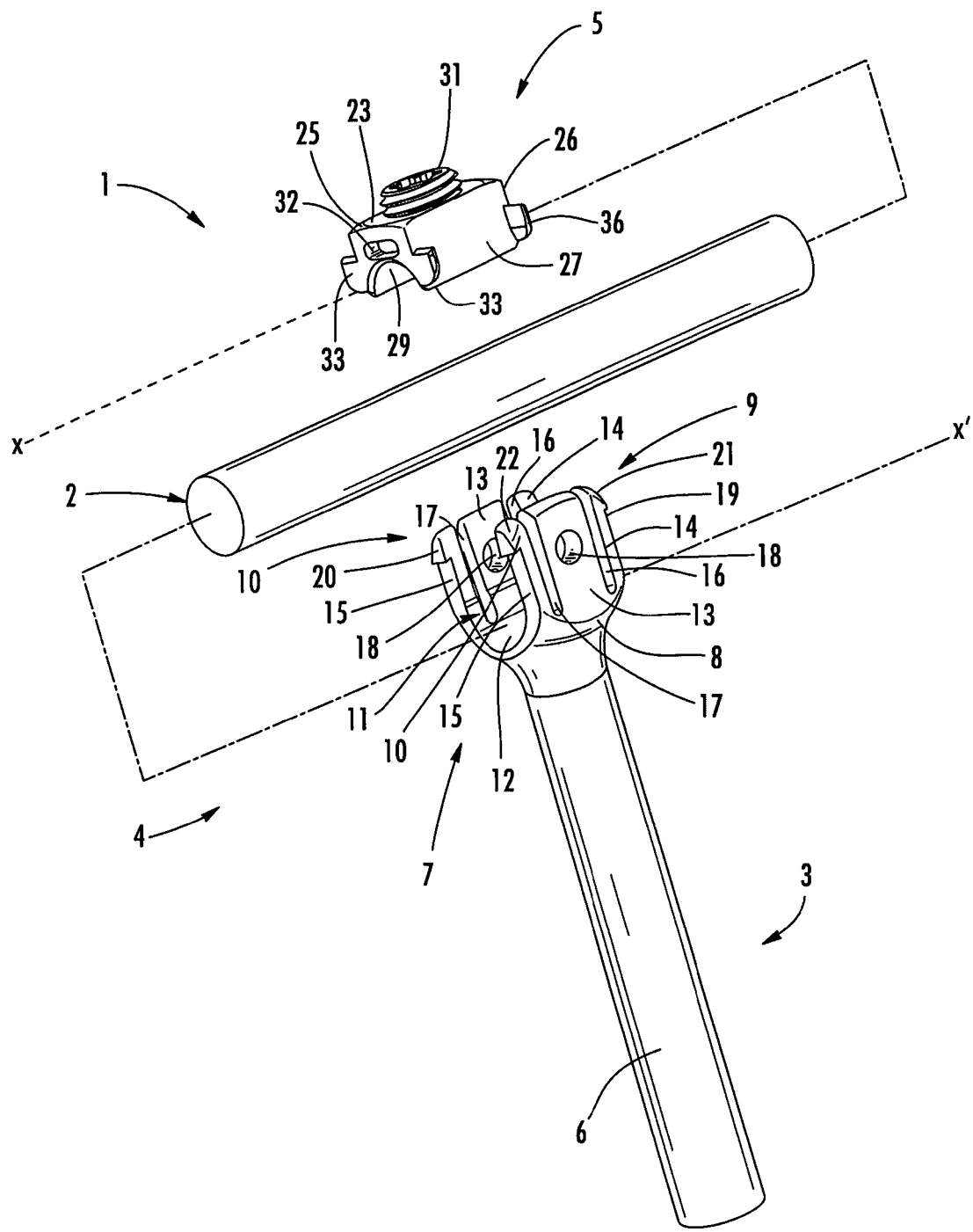
FIG. 1 is an exploded perspective view showing the immobilization device according to the present invention.

There is shown in FIG. 1 an immobilization device 1 of a rachidian implant 4 for blocking in rotation and translation a connecting rod 2 in each vertebra belonging to a vertebral column.

The immobilization device 1 is constituted by an osseous anchoring element 3 and a blocking element 5 adapted to coact with the anchoring element 3 to secure in rotation and in translation the connecting rod 2.

Figure 2:
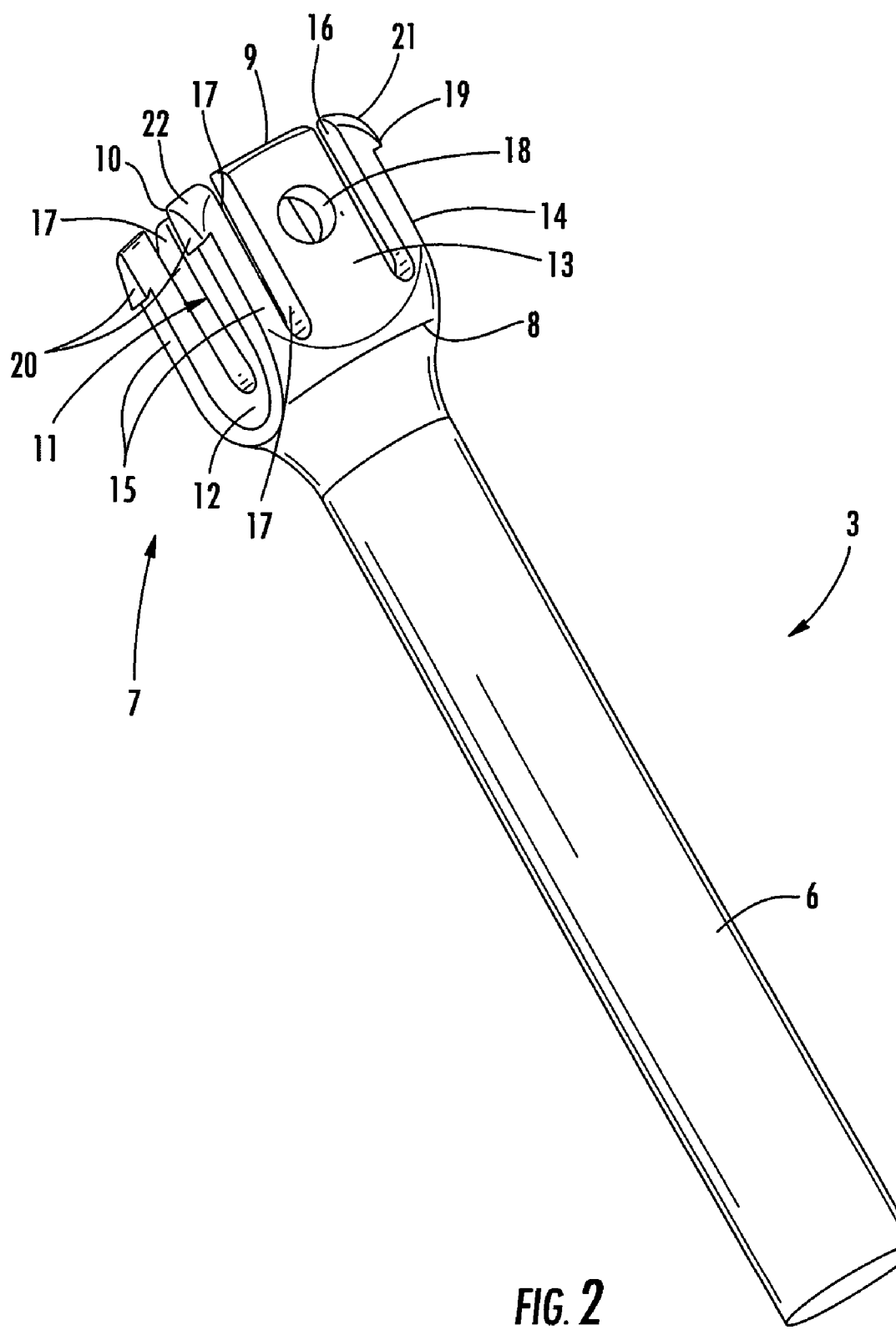
FIG. 2 is a perspective view showing the osseous anchoring element of the immobilization device according to the present invention.

There is shown in FIG. 2 the osseous anchoring element 3 comprising an anchoring portion 6 and a reception portion 7.

The anchoring portion 6 can have either the form of a hook, or a screw-threaded profile secured or not to the reception portion 7 to be fixed on or in the vertebral body of a vertebra to be equipped.

The reception portion 7 is constituted by a head 8 of U shape open at its upper portion 7 to be able to coact with the connecting rod 2 and the blocking element 5.

The head 8 comprises two vertical walls 9, 10 disposed facing each other and in parallel planes so as to delimit a central opening 11 of U shape whose bottom 12 has a part cylindrical profile.

Each vertical wall 9, 10 is constituted by a central surface 13 bordered laterally and on each side by elastic blades 14, 15 separated respectively from said central surface by vertical slots 16, 17.

The central surface 13 of each vertical wall 9, 10 is pierced with a hole 18 opening within the central opening 11 of U shape.

The elastic blades 14, 15 of the head 8 comprise respectively in their upper portion a tooth 19, 20 whose external profile 21, 22 is convexly curved and inclined in the outward direction of each vertical wall 9, 10.

Figure 3:
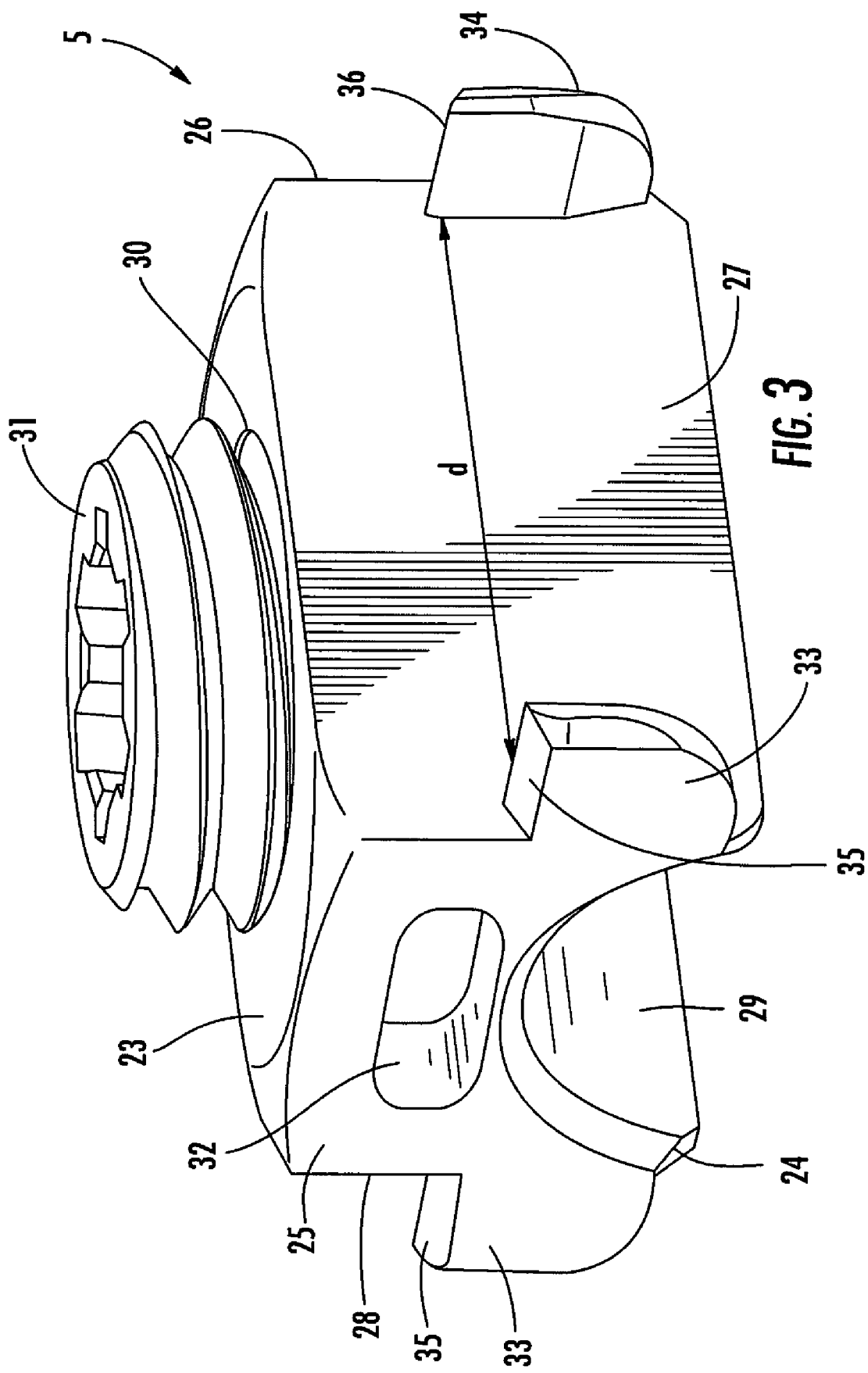
FIG. 3 is a perspective view showing the element for blocking in translation and rotation the connecting rod within the osseous anchoring element of the immobilization device according to the present invention.

There is shown in FIG. 3 the blocking element 5 of the immobilization device 1 which has an external profile that is substantially parallelepipedal, of which each of the opposite surfaces 23, 24; 25, 26, 27 and 28 are parallel two by two.

Thus the lower surface 24 of the blocking element 5 comprises in a direction parallel to the axis XX' of the connecting rod 2, a seat 29 having a part cylindrical profile.

The upper surface 23 of the blocking element 5 comprises at its middle a screw-threaded bore 30 opening within the seat 29 and in which coacts a tightening screw 31.

The first pair of lateral surfaces 25, 26 of the blocking element 5 comprises respectively above the seat 29 an impression 32 adapted to coact with the teeth of an instrument (not shown) permitting the manipulation and the emplacement of said blocking element on the osseous anchoring element 3.

The second pairs of lateral surfaces 27, 28 of the blocking element 5 are each secured to two lugs 33, 34 disposed in the width of said blocking element, namely in prolongation of each lateral surface 25, 26.

Thus, the blocking element 5 comprises four lugs 33, 34 extending in the outward direction of this latter and in a direction perpendicular to the plane containing each lateral surface 27, 28.

Each lug 33, 34 comprises respectively in its lower portion an inclined flat or bevel 35, 36 directed in the direction of the lateral surfaces 25, 26 such that the lower base of each inclined flat 35, 36 will be in the plane containing each of said lateral surfaces 25, 26.

Each lug 33, 34 comprises respectively in its lower portion and opposite the inclined flats 35, 36 a rounded profile 37, 38 permitting the sliding of said lugs on said teeth 19, 20 during assembly of the blocking element 5 with the osseous anchoring element 3.

The distance d provided between two lugs 33, 34 of a same lateral surface 27, 28 is less than that provided between two teeth 19, 20 of a same vertical wall 9, 10 of the head 8 of the osseous anchoring element 3.

Figure 4:
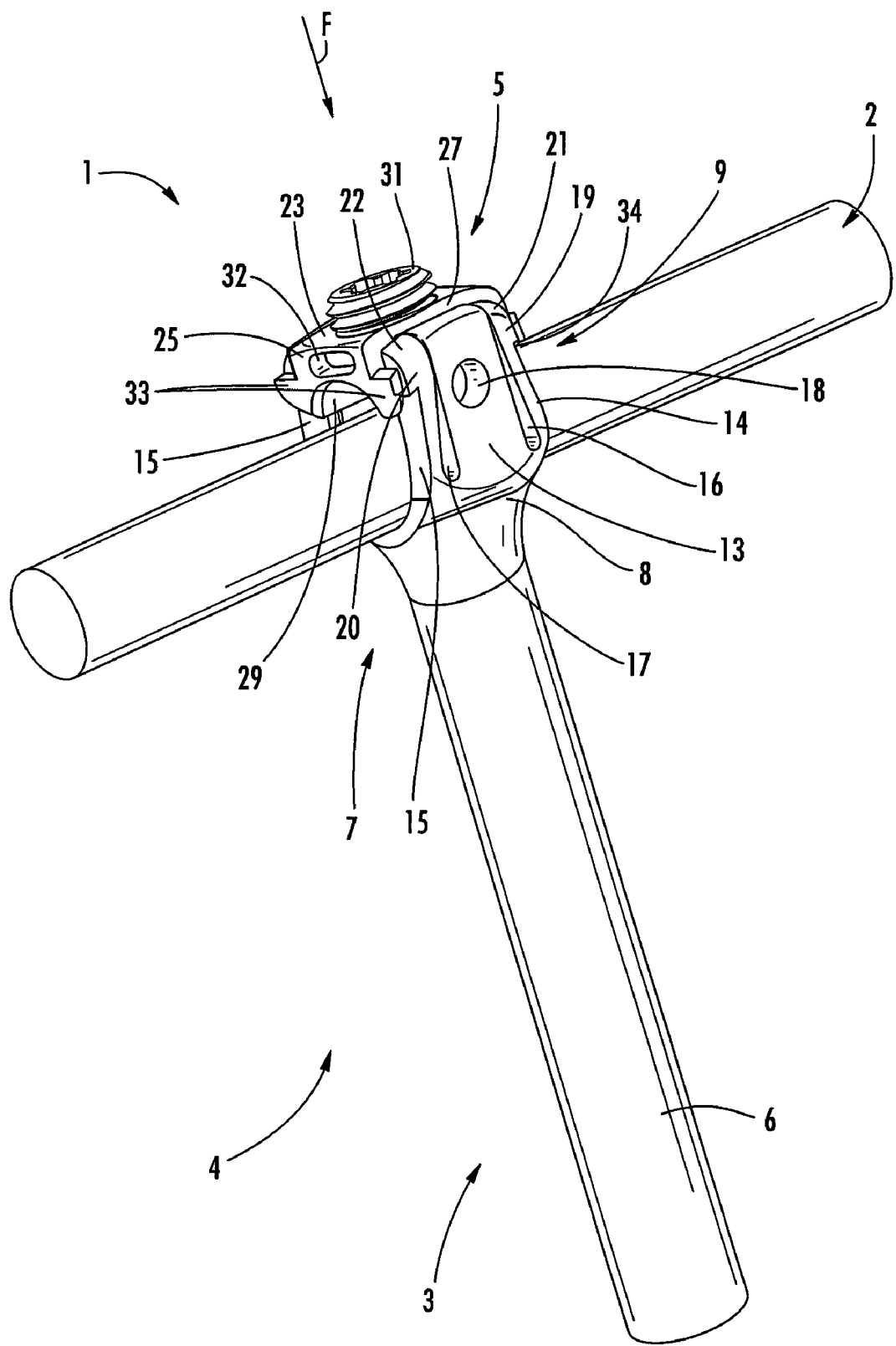
FIG. 4 is a perspective view showing the elastic deformation of the osseous anchoring element during mounting of the blocking element of the immobilization device according to the present invention.
Figure 5:
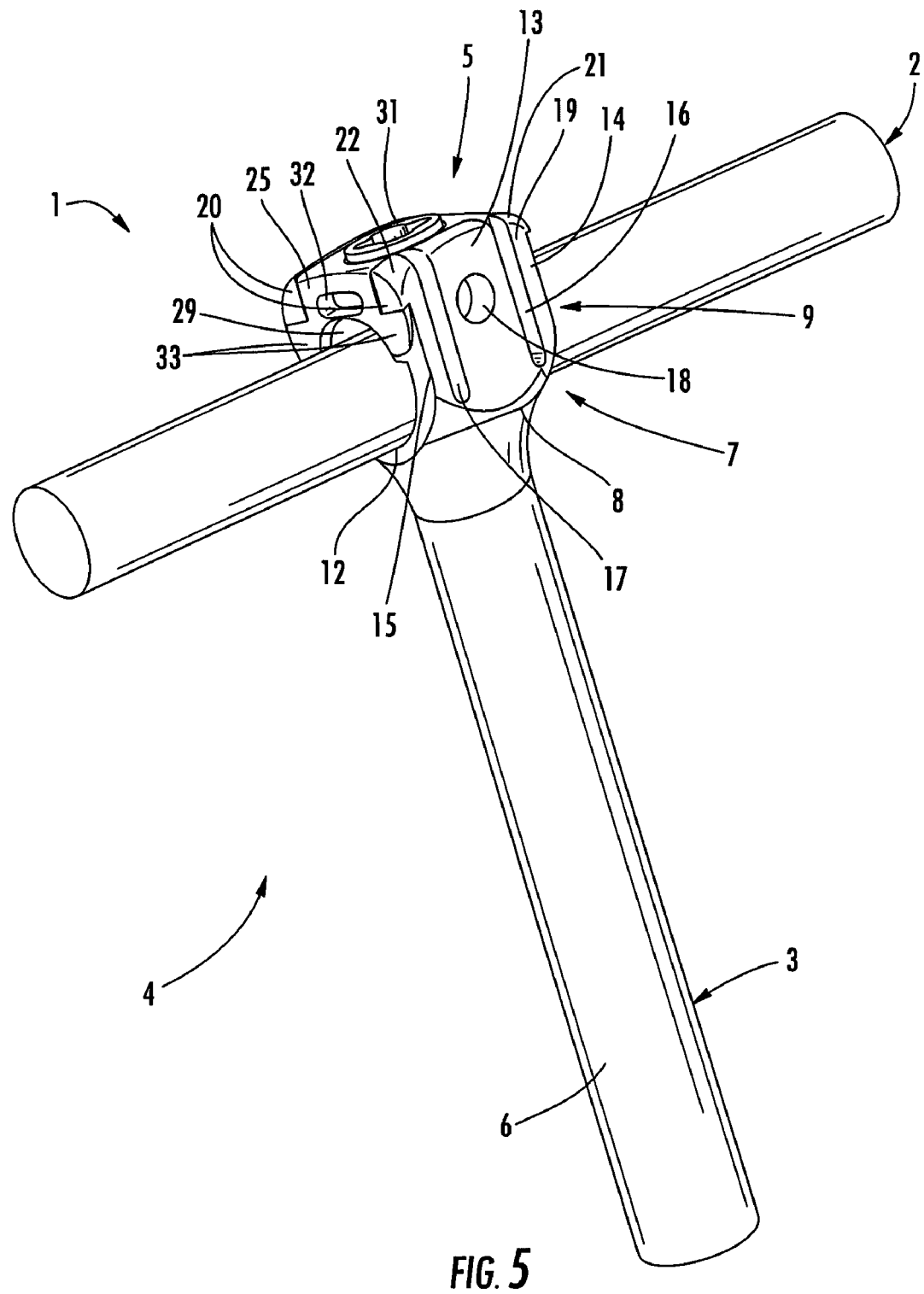
FIG. 5 is a perspective view showing the immobilization device in the assembled position for blocking in rotation and translation the connecting rod of the rachidian implant.
Figure 6:
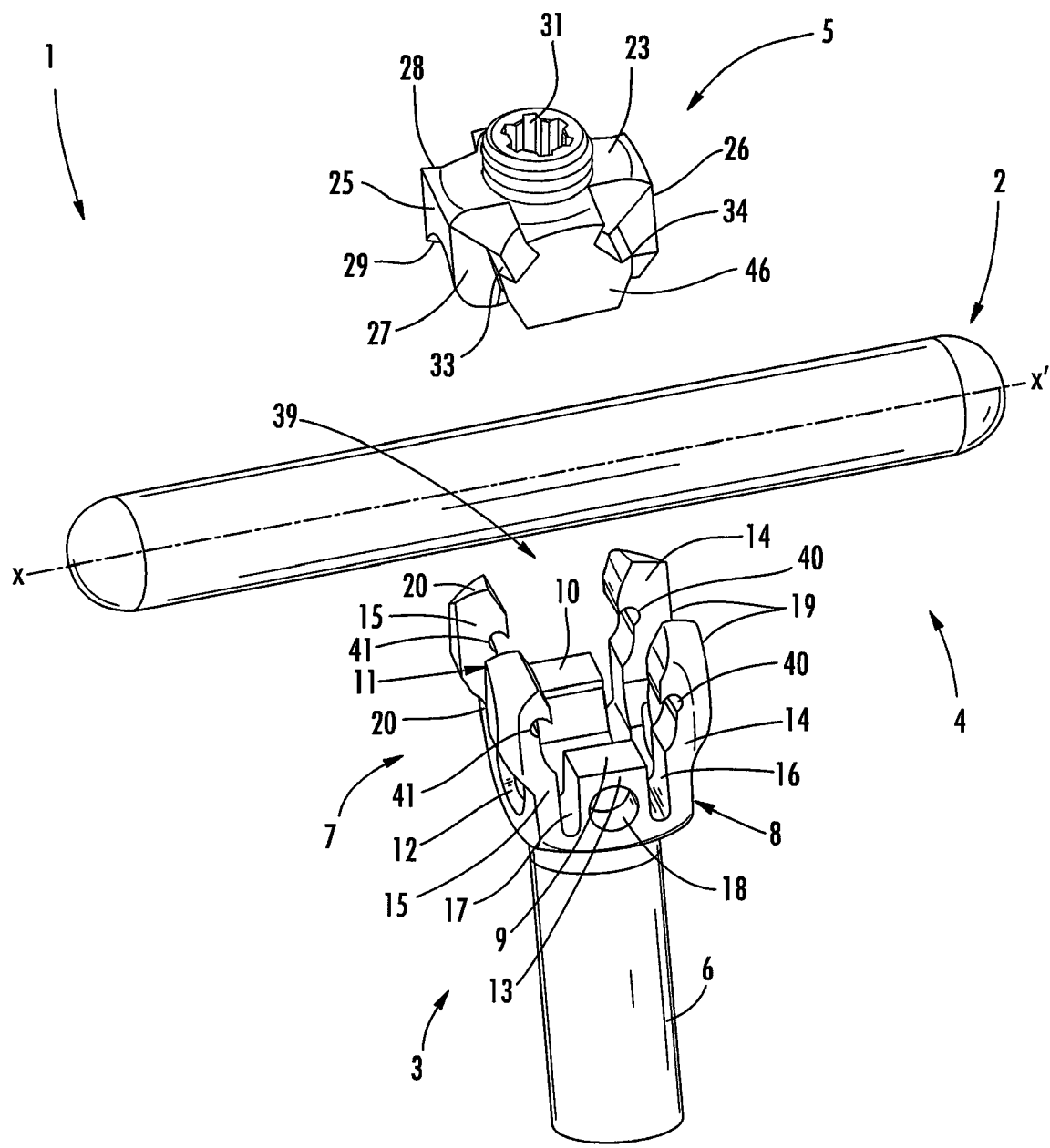
FIG. 6 is an exploded perspective view showing the first modification of the immobilization device according to the present invention.

There is shown in FIGS. 4 and 5 the emplacement and retention of the blocking element 5 on the head 8 of the anchoring element 3 so as to be able to block in rotation and in translation the connecting rod 2 in each anchored immobilization device 1 of the vertebral body of a vertebra.

The osseous anchoring element 3 is fixed or hooked as a function of its structure to the vertebral body of a vertebra to be equipped.

The connecting rod 2 is positioned within the central opening 11 of the head 8 of the osseous anchoring element 3.

The blocking element 5 is positioned above the head 8 of the osseous anchoring element 3 such that the lugs 33, 34 of a same lateral surface 27, 28 come to bear against the corresponding teeth 19, 20 of a same vertical wall 9, 10.

A pressure force F is applied with the help of an instrument (not shown) to the blocking element 5 such that the lugs 33, 34 of each lateral surface 27, 28 define laterally the elastic blades 14, 15 of each wall 9, 10 of the head 8 of the osseous anchoring element 3.

The elastic deformation of the blades 14, 15 takes place in the direction of the central surface 13 of each vertical wall 9, 10 of the head 8 because of the difference in width provided between the lugs 33, 34 and the teeth 19, 20 (FIG. 4).

The introduction of the blocking element 5 is facilitated by the fact that each lug 33, 34 has a lower portion of rounded profile 37, 38 which slides on the external convexly rounded profile 21, 22 of each tooth 19, 20 secured to the blades 14, 15.

The pressure force F must be sufficient that each lug 33, 34 comes into snap fitting engagement with the corresponding tooth 19, 20 of the elastic blades 14, 15. The retention of the lugs 33, 34 is obtained when each inclined flat 35, 36 coacts with the profile of the corresponding tooth 19, 20 (FIG. 5).

Also, the retention of the lugs 33, 34 is obtained by the elasticity of the blades 14, 15 which return to the rest position after the passage of the lugs 33, 34 over the corresponding teeth 19, 20.

The connecting rod 2 is then immobilized in rotation and in translation by means of the tightening screw 31 which is screwed within the bore 30 of the blocking element 5. The tightening screw 31, under the screwing force, blocks the connecting rod 2 against the part cylindrical bottom 12 of the central opening 11 of the head 8 of the anchoring element 3.

Also, the tightening force of the pressure screw 31 against the connecting rod 2 permits, by means of vertical displacement directed in a direction opposite that of said rod, to block the blocking element 5 in the head 8 of the anchoring element 3.

There is shown in FIGS. 6 to 10 a first modification of the rachidian implant and more particularly of the immobilization device 1 for the blocking in rotation and translation of the connecting rod 2 in each equipped vertebra of a vertebral column.

For purposes of clarity, the elements identical to those previously described have the same reference number so as to avoid any confusion.

The immobilization device 1 is constituted by an osseous anchoring element 3 and a blocking element 5 adapted to coact with the anchoring element 3 for the securement in rotation and in translation of the connecting rod 2.

Figure 7:
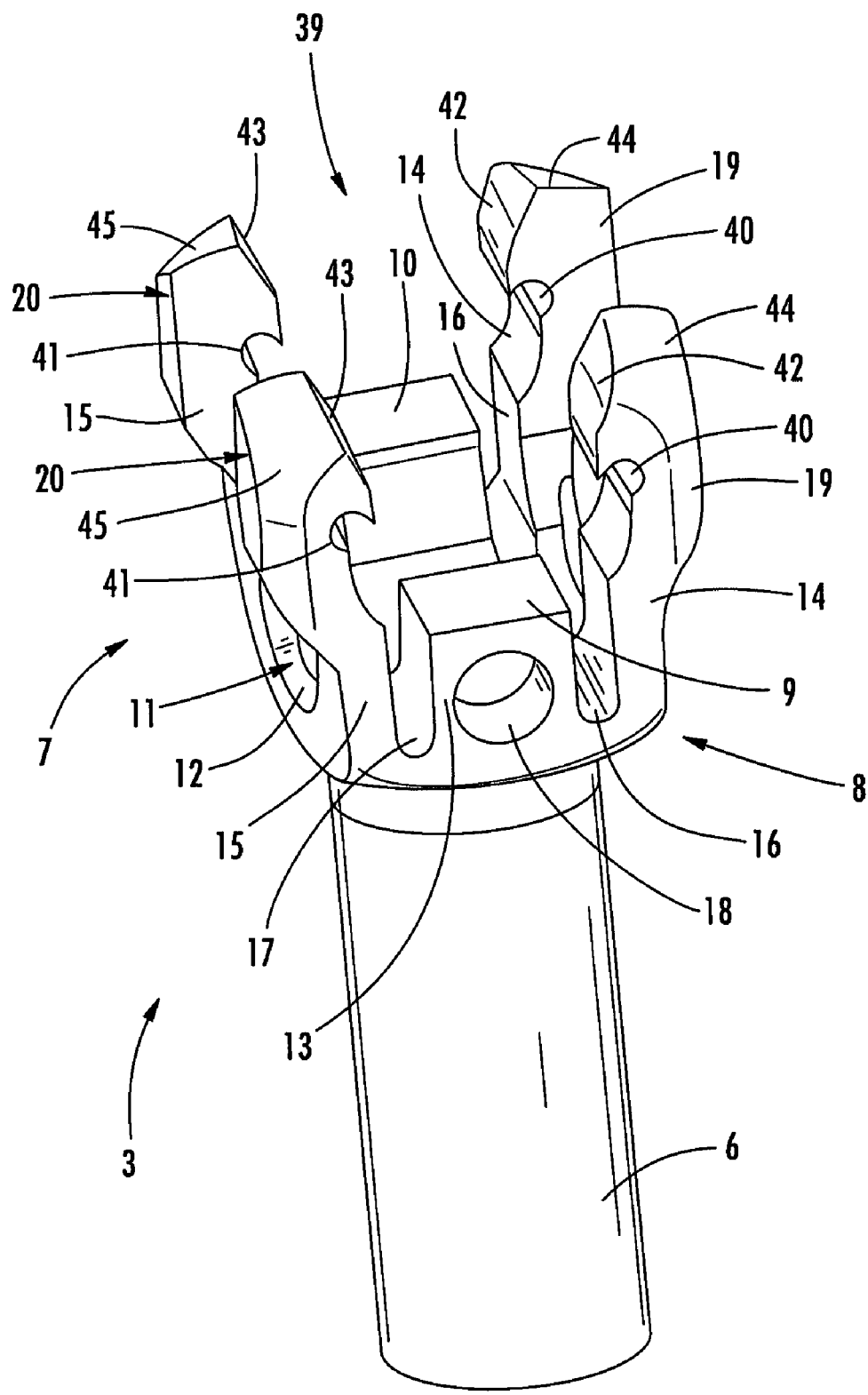
FIG. 7 is a perspective view showing the osseous anchoring element of the first variation of the immobilization device according to the present invention.

There is shown in FIG. 7 the osseous anchoring element 3 comprising an anchoring portion 6 and a reception portion 7. The anchoring portion 6 can have either the form of a hook, or a screw-threaded profile secured or not to the reception portion 7 to be fixed on and/or in the vertebral body of a vertebra to be equipped.

The reception portion 7 is constituted by a U shaped head 8, open in its upper portion to be able to coact with the connection rod 2 and the blocking element 5.

The head 8 comprises two vertical walls 9, 10 of truncated profile, disposed one facing the other and in parallel planes so as to delimit a first central opening 11 of U shape carried by the axis XX' of the connecting rod 2 and whose bottom 12 has a part cylindrical profile, and a second opening 39 perpendicular to the axis XX' and to the first opening 11.

The two perpendicular openings 11 and 39 permit delimiting at each angle the head 8 of the retaining means 14, 15 adapted to deform elastically under the pressure force F.

Each truncated vertical wall 9, 10 is constituted by a central surface 13 whose height is delimited by the second opening 39 passing through the head 8 of the reception portion 7.

Each central surface 13 is bordered laterally and on each side by elastic blades 14, 15 separated respectively from said central surface by vertical slots 16, 17.

The central surface 13 of each truncated vertical wall 9, 10 is pierced by a blind hole 18 permitting an instrument to hook to permit the introduction of the blocking element 5 in the anchoring element 3.

The elastic blades 14, 15 of the head 8 comprise respectively in their upper portion a tooth 19, 20 whose hooking profile 40, 41 is turned in the internal direction of the second opening 39 and above the central surface 13 of each vertical wall 9, 10.

Each tooth 19, 20 comprises above its hooking portion 40, 41 and in the opening direction 39, an inclined external profile 42, 43 prolonged in the outward direction of each blade 14, 15 by a convexly rounded profile 44, 45.

Figure 8:
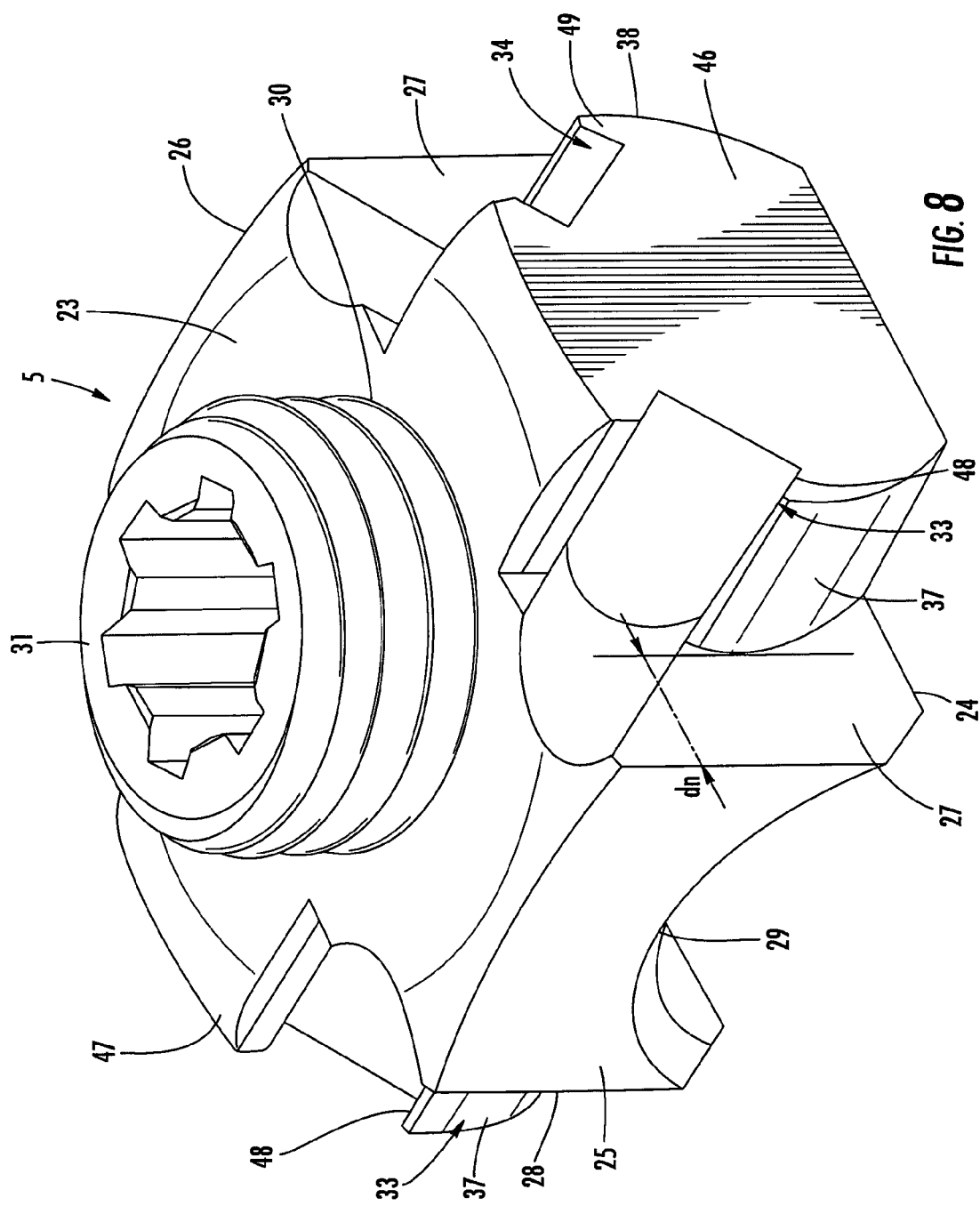
FIG. 8 is a perspective view showing the element for blocking in translation and rotation of the connecting rod within the osseous anchoring element of the first modification of the immobilization device according to the present invention.

There is shown in FIG. 8 the blocking element 5 of the immobilization device 1 which has a substantially parallelepipedal external profile of which all of the opposite surfaces 23, 24; 25, 26, 27 and 28 are parallel two by two.

Thus, the lower surface 24 of the blocking element 5 comprises in a direction parallel to the axis XX' a seat 29 having a part cylindrical profile so as to receive the connecting rod 2 during mounting and securement of the immobilization device 1.

The upper surface 23 of the blocking element 5 comprises at its middle a screw-threaded bore 30 opening within the seat 29 and in which coacts a tightening screw 31.

Each lateral surface 27, 28 disposed in a plane parallel to the axis XX' of the seat 29 and perpendicular to each of the external surfaces 25, 26 of the blocking element 5, is secured to an increased thickness 46, 47 delimiting two lugs 33, 34 in the form of teeth.

Thus, the blocking element 5 comprises two lugs 33 and two lugs 34 which extend in the external direction of this latter.

Each lug 33, 34 comprises respectively a hooking portion 48, 49 delimited by an arrangement of inclined and convexly rounded profiles permitting coaction with the hooking portions 40, 41 of each tooth 19, 20 during emplacement of the blocking element 5 in the head 8 of the anchoring element 3.

It is to be noted that the hooking portions 48, 49 of each lug 33, 34 are positioned retracted and at a distance d1 from the lateral and opposed surfaces 25, 26 of the blocking element 5.

Each lug 33, 34 has respectively an inclined external profile 37, 38 permitting sliding of said lugs and the spacing of the elastic blades 14, 15 outwardly of the head 8 so as to be able to provide the assembly of the blocking element 5 with the osseous anchoring element 3.

Figure 9:
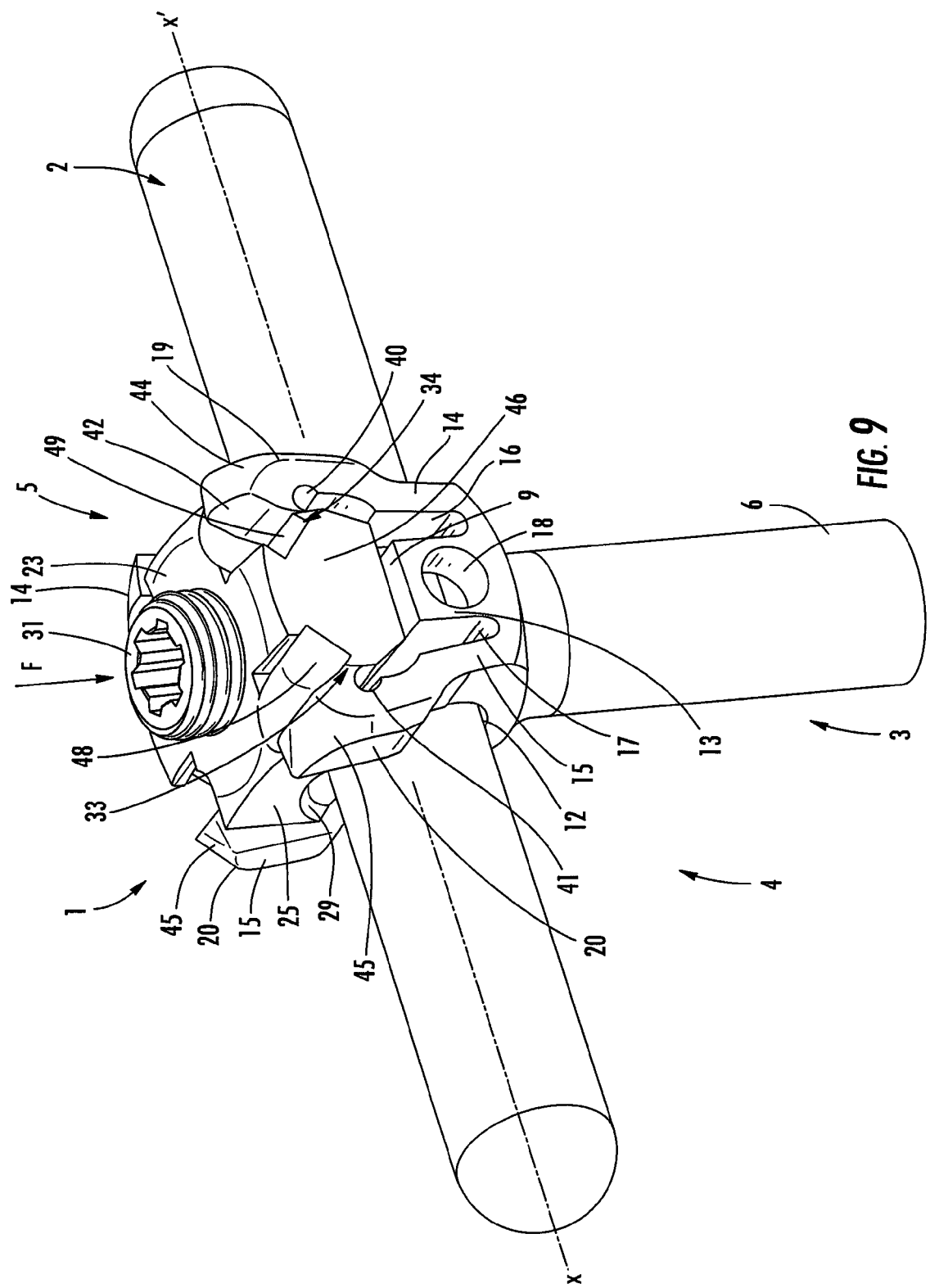
FIG. 9 is a perspective view showing the elastic deformation of the osseous anchoring element during mounting of the blocking element of the first modification of the immobilization device according to the present invention.
Figure 10:
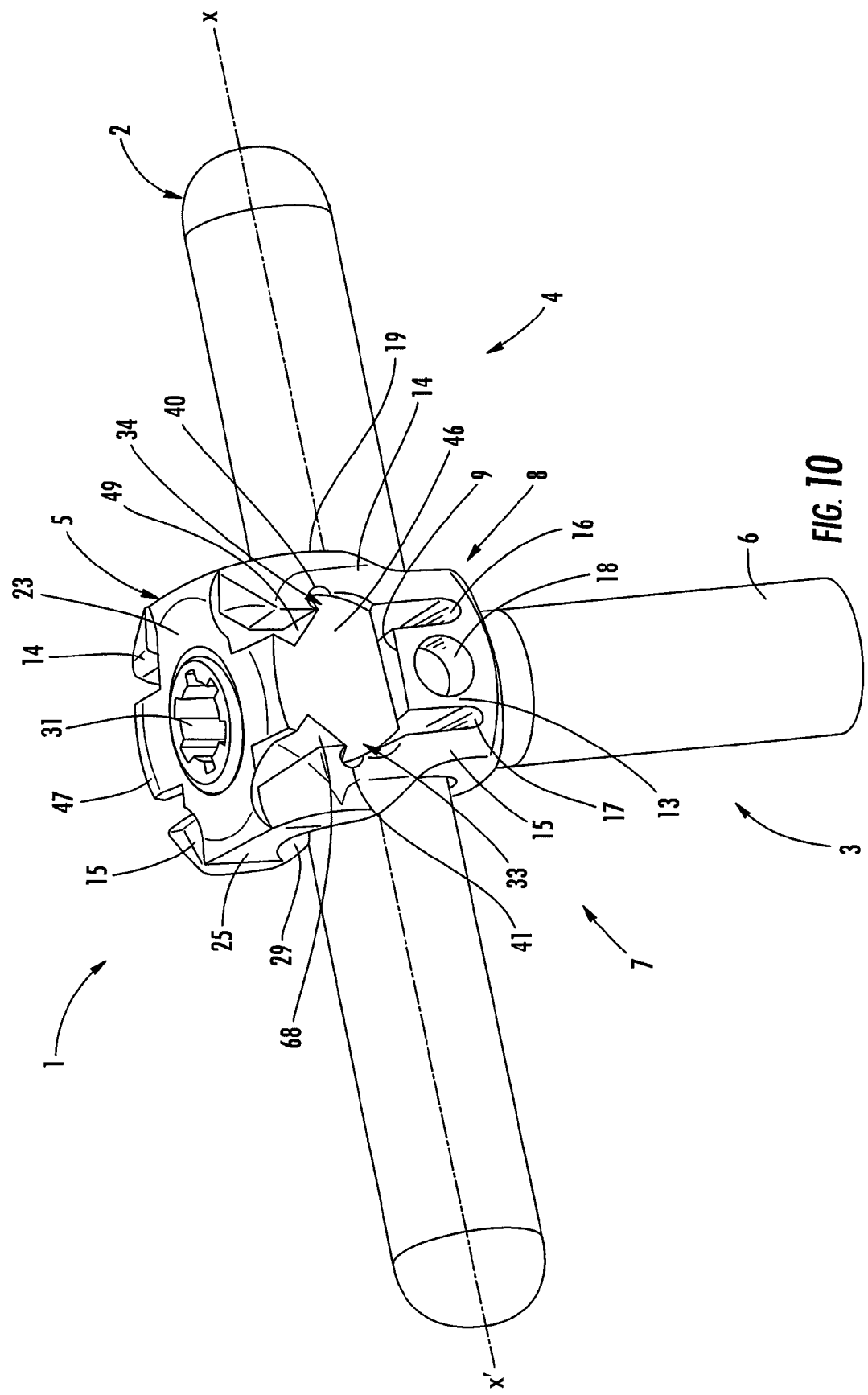
FIG. 10 is a perspective view showing the first modification of the immobilization device in the assembled position for blocking in rotation and translation the connecting rod of the rachidian implant.
Figure 11:
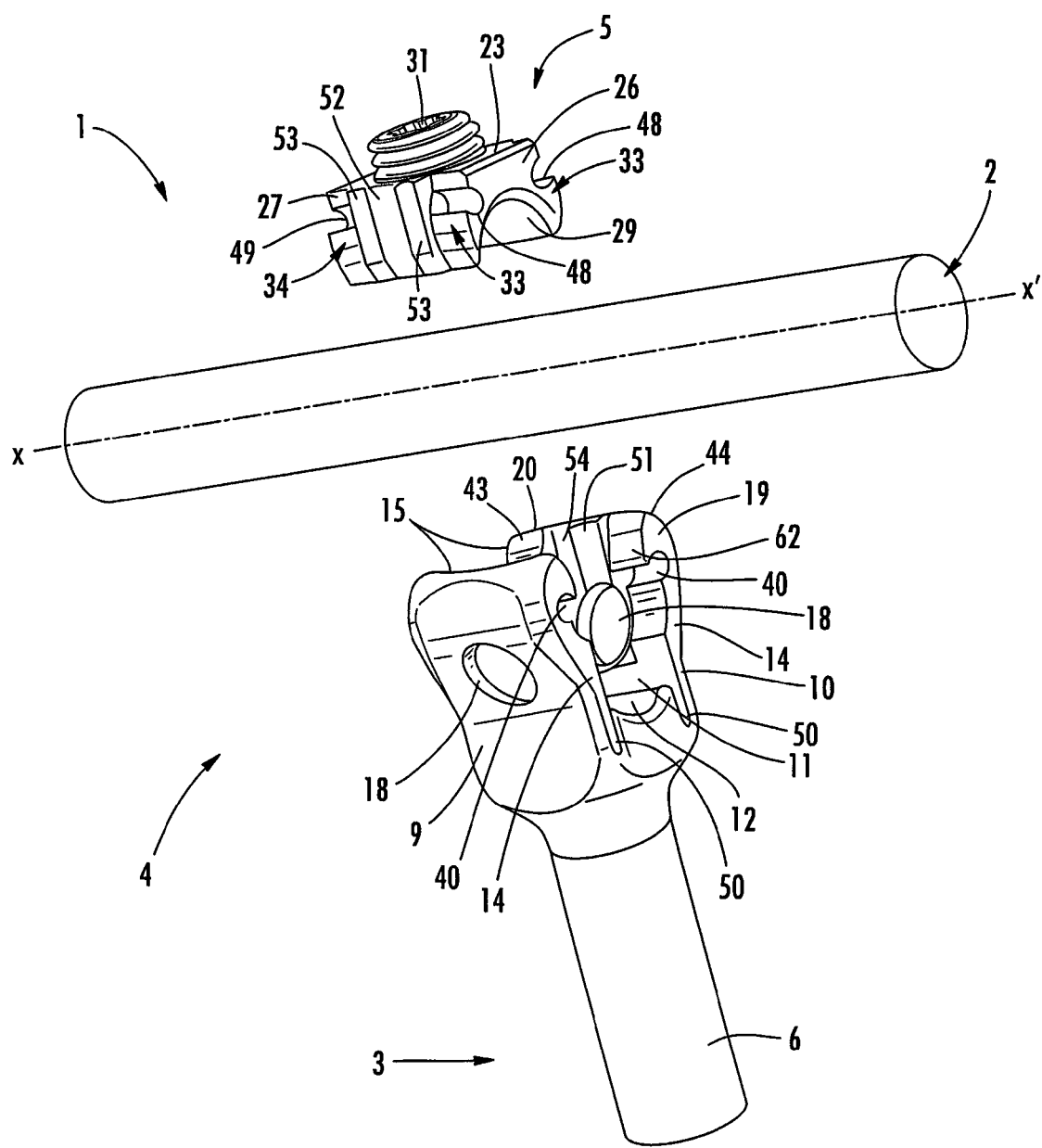
FIG. 11 is an exploded perspective view showing a second modification of the immobilization device according to the present invention.
Figure 12:
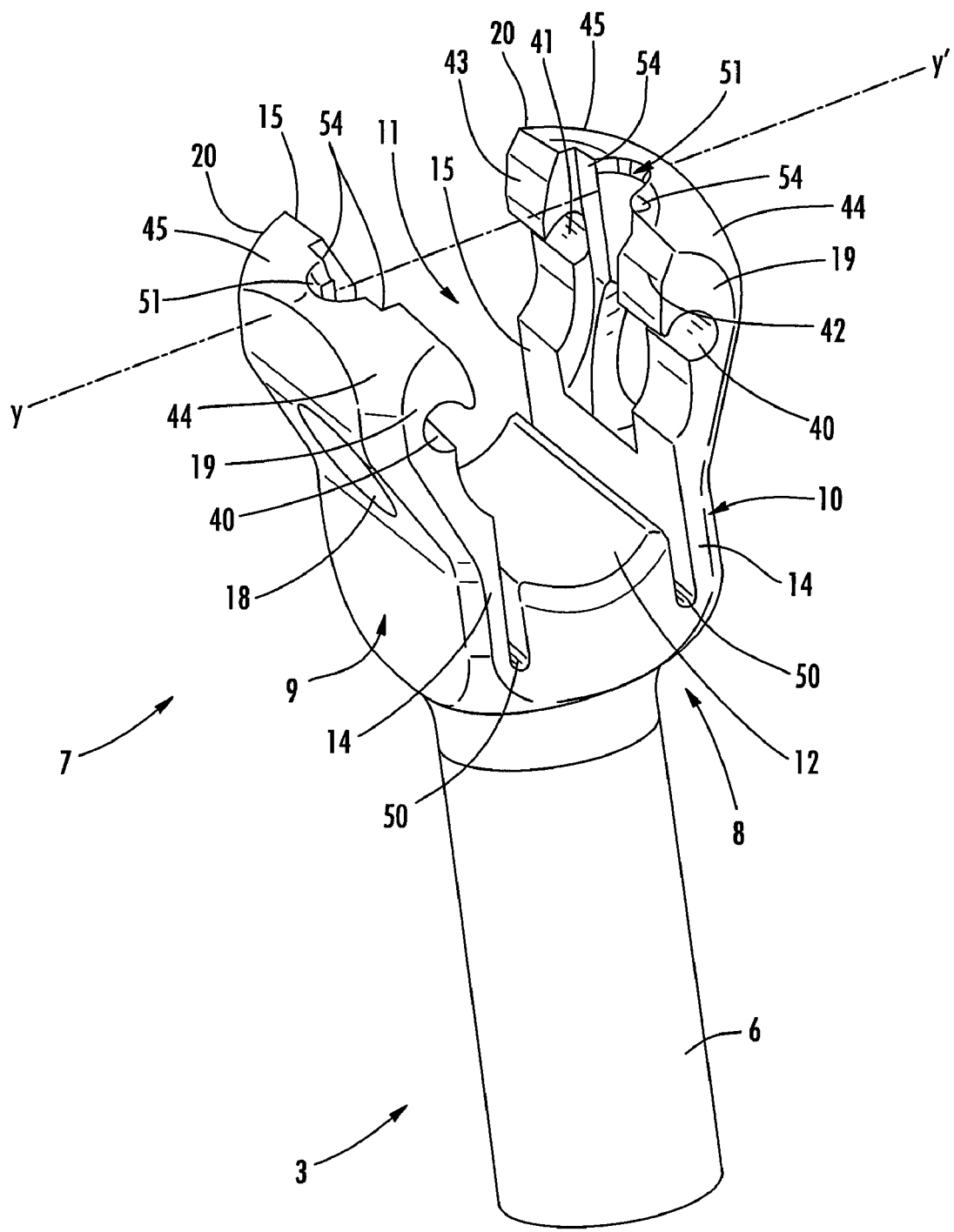
FIGS. 12 and 13 are perspective views showing the osseous anchoring element of the second modification of the immobilization device according to the present invention.
Figure 13:
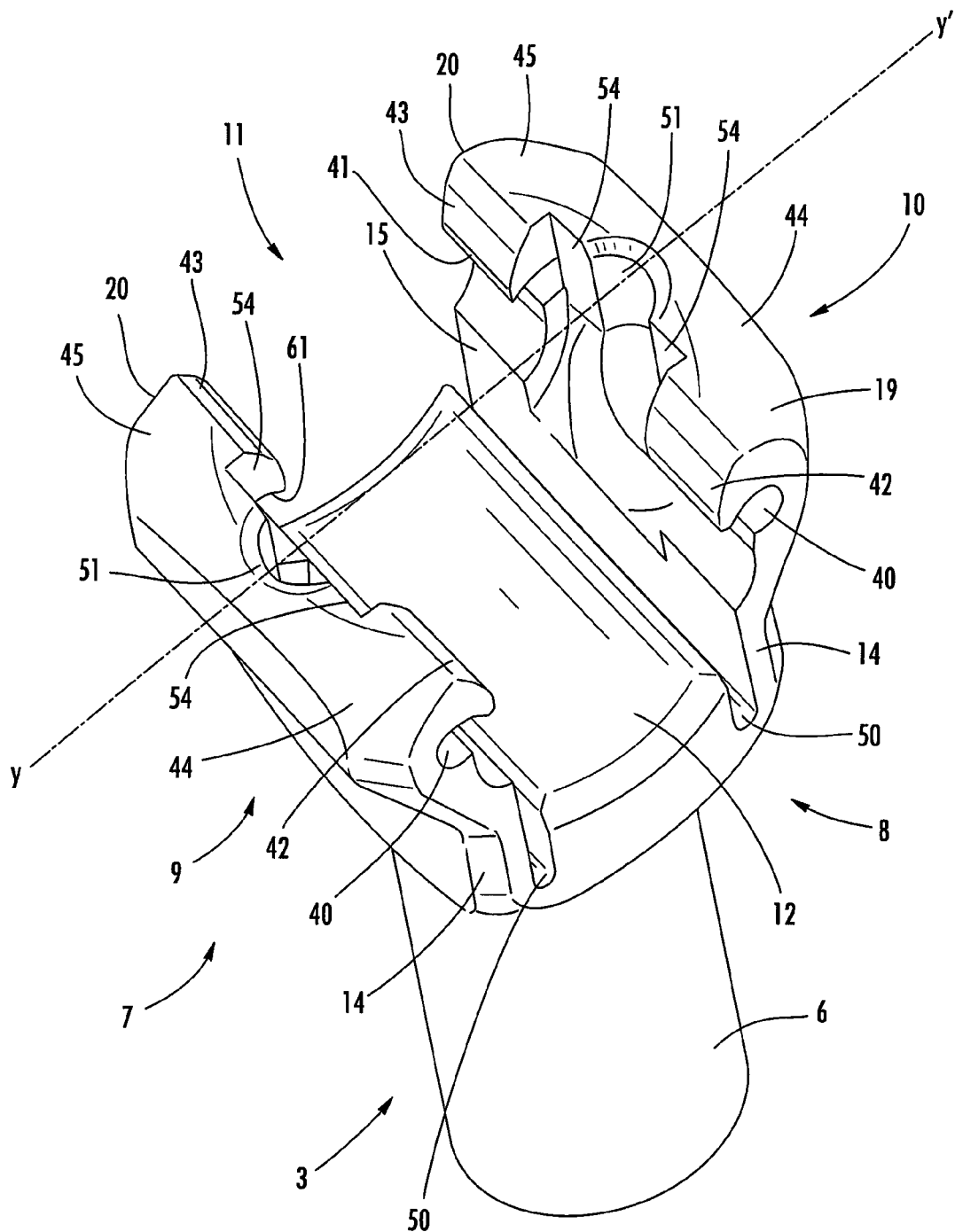

There is shown in FIGS. 9 and 10 the different steps permitting the assembly of the blocking element 5 in the head 8 of the anchoring element 3 for the securement in rotation and in translation of the connecting rod 2 in each immobilization device 1 anchored in the vertebral body of a vertebra.

The osseous anchoring element 3 is fixed or hooked as a function of its structure to a vertebra to be equipped.

The connecting rod 2 is positioned within the central opening 11 of the head 8 and of the osseous anchoring element 3 before introduction of the blocking element 5.

The blocking element 5 is positioned above the head 8 of the osseous anchoring element 3 such that the lugs 33, 34 of a same lateral surface 27, 28 come to bear against the corresponding teeth 19, 20 of a same vertical wall 9, 10.

A pressure force F is produced in a substantially vertical direction, with an instrument (not shown), on the blocking element 5, so that the lugs 33, 34 of each lateral surface 27, 28 deform laterally the elastic blades 14, 15 of each wall 9, 10 of the head 8 of the osseous anchoring element 3.

The elastic deformation of the blades 14, 15 takes place in an outward direction of the head 8, which is to say in a direction which spaces the central surface 13 of each vertical wall 9, 10 from the head 8, because of the difference of the dimensions provided between the lugs 33, 34 and the teeth 19, 20 (FIG. 9).

The introduction of the blocking element 5 is facilitated by the fact that each lug 33, 34 has a lower portion with an inclined profile 37, 38 which slides on the external profile of each tooth 19, 20 secured to the blades 14, 15.

The pressure force F must be sufficient that each hooking portion 48, 49 of the lugs 33, 34 comes into snap-fitting engagement with the hooking portion 40, 41 of each corresponding tooth 19, 20 of the elastic blades 14, 15.

The retention of the blocking element 5 is achieved by the elasticity of the blades 14, 15, which return to the rest position after the passage of the lugs 33, 34 over the corresponding teeth 19, 20.

The connection rod 2 is adjusted by sliding in a cylindrical trough constituted by the bottom 12 having a part cylindrical profile of the head 8 of the osseous anchoring element 3 and the seat 29 having a part cylindrical profile of the blocking element 5.

The connecting rod 2 is then immobilized in rotation and in translation by means of the tightening screw 31 which is screwed within the bore 30 of the blocking element 5. The tightening screw 31, under the screwing force, blocks the connecting rod 2 against the part cylindrical bottom 12 of the central opening 11 of the head 8 of the anchoring element 3.

Also, the tightening force of the pressure screw 31 against the connecting rod 2 permits, by means of vertical movement directed in a direction opposite that of said rod, to block the blocking element 5 in the head 8 of the anchoring element 3.

There is shown in FIGS. 11 to 18 a second modification of the rachidian implant and more particularly of the immobilization device 1 for blocking in rotation and translation a connecting rod 2 in each equipped vertebra of a vertebral column.

For purposes of clarity, the elements identical to those previously described have the same reference numerals.

The immobilization device 1 is constituted by an osseous anchoring element 3 and a blocking element 5 adapted to coact with the anchoring element 3 for the securement in rotation and in translation of the connecting rod 2.

The osseous anchoring element 3 comprises an anchoring portion 6 and a reception portion 7. The anchoring portion 6 can have either the form of a hook, or a screw-threaded profile secured or not to the reception portion 7 to be fixed on or in the vertebra to be equipped.

The reception portion 7 is constituted by a U shaped head 8 open in its upper portion to be able to coact with the connection rod 2 and the blocking element 5.

The head 8 comprises two vertical walls 9, 10 disposed facing each other and in parallel planes so as to delimit a first central U shaped opening 11 carried by the axis XX' of the connecting rod 2 and whose bottom 12 has a part cylindrical profile.

Each vertical wall 9, 10 is separated from the bottom 12 of the central opening 11 by a vertical slot 50 imparting a certain elasticity to each wall in a direction YY' perpendicular to the direction XX' of the connecting rod 2.

The elastic vertical walls 9, 10 comprise respectively at each end a profile in the form of a hooking blade 14, 15 disposed facing each other on opposite sides of the central opening 11.

Each elastic vertical wall 9, 10 comprises on its internal surface and between the hooking blades 14, 15, a vertical seat 51 having a part-cylindrical profile.

The vertical seat 51 has on each side a groove 54 permitting guiding the blocking element 5 during its emplacement within the U shaped head 8.

Each elastic vertical wall 9, 10 is pierced between the hooking blades 14, 15 by a hole 18 opening within the central opening 11 permitting an instrument to hook to permit the introduction of the blocking element 5 in the anchoring element 3.

The hooking blades 14, 15 of the head 8 comprise respectively in the upper portion a tooth 19, 20 whose hooking profile 40, 41 is turned in the direction of the interior of the central opening 11.

Each tooth 19, 20 comprises above its hooking portion 40, 41 an inclined external portion 42, 43 prolonged in the outward direction of each blade 14, 15 by a convexly rounded profile 44, 45.

Figure 14:
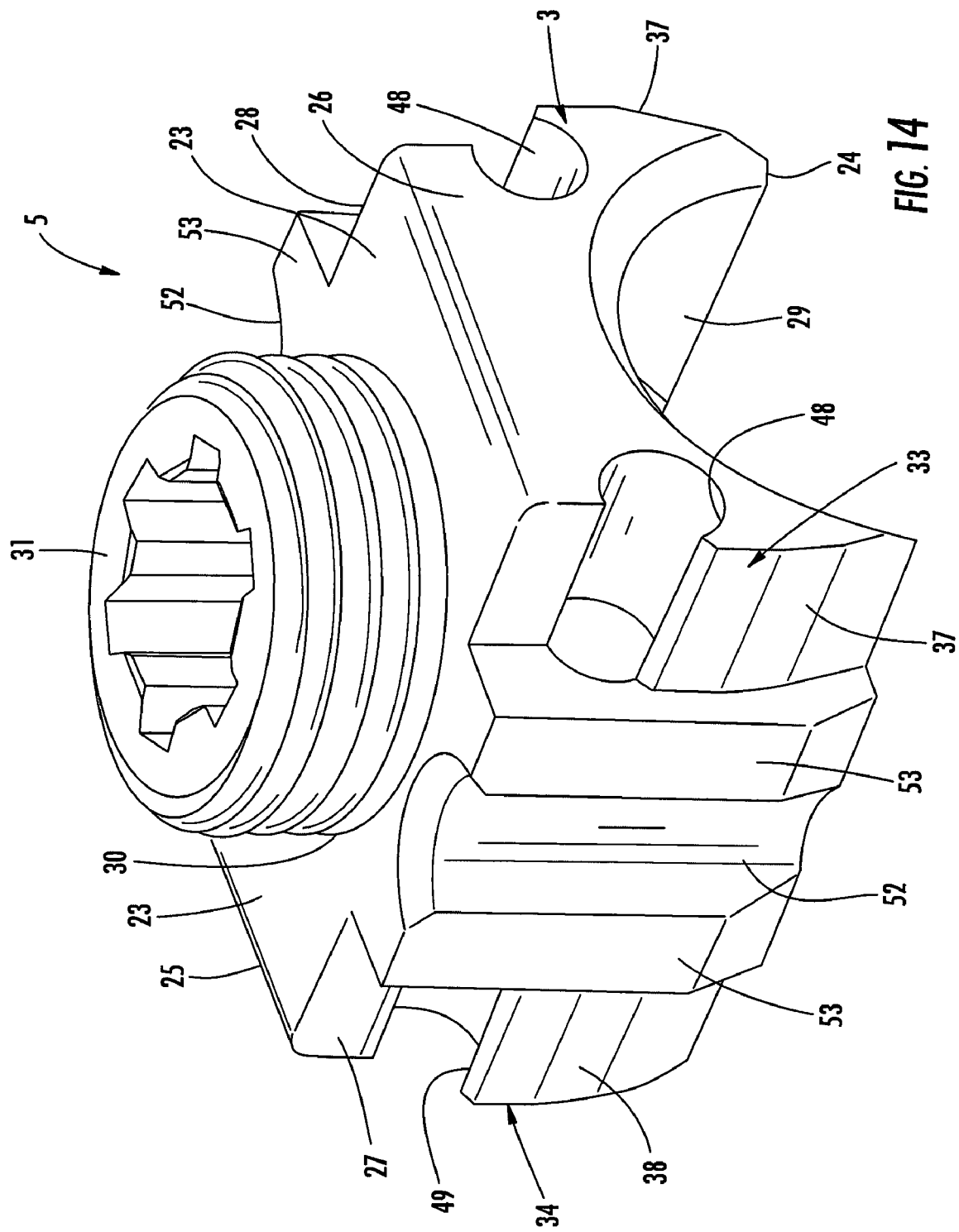
FIG. 14 is a perspective view showing the element for blocking in translation and rotation the connecting rod within the osseous anchoring element of the second modification of the immobilization device according to the present invention.

There is shown in FIG. 14 the blocking element 5 of the immobilization device 1 which has a substantially parallelepipedal external profile of which all of the opposite surfaces 23, 24; 25, 26, 27 and 28 are parallel two by two.

Thus, the surface 24 of the blocking element 5 comprises in a direction parallel to the axis XX' a seat 29 having a part cylindrical profile so as to receive the connecting rod 2 during mounting and securement of the immobilization device 1.

The upper surface 23 of the blocking element 5 comprises at its middle a screw-threaded bore 30 opening within the seat 29 and in which coacts a tightening screw 31.

Each lateral surface 27, 28 disposed in a plane parallel to the axis XX' of the seat 29 and perpendicular to each of the lateral surfaces 25, 26 of the blocking element 5, comprises two lugs 33, 34 in the form of teeth.

Thus, the blocking element 5 comprises two lugs 33 and two lugs 34 which extend in the outward direction of this latter.

Figure 15:
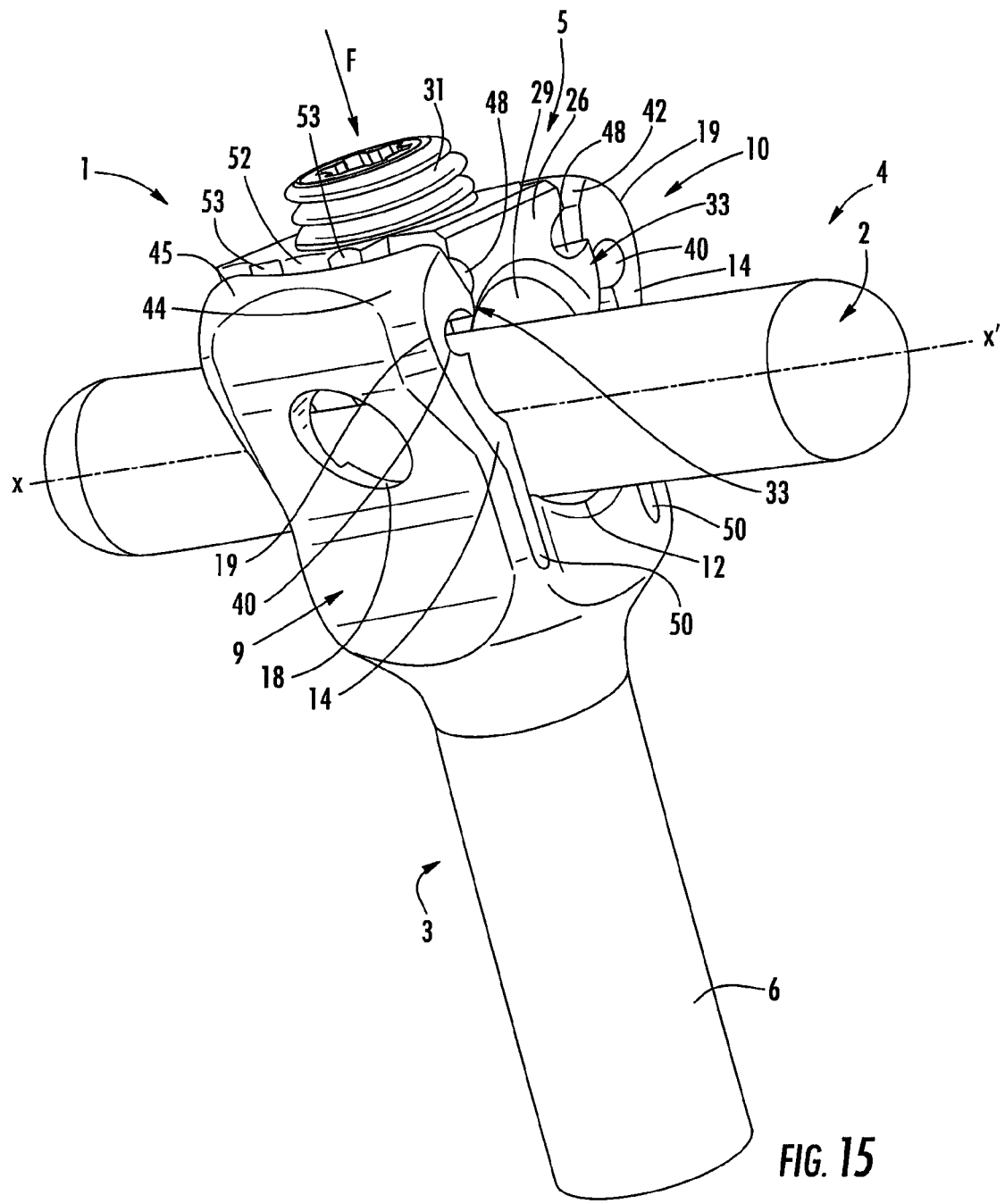
FIGS. 15 and 16 are views showing the elastic deformation of the osseous anchoring element during mounting of the blocking element of the second modification of the immobilization device according to the present invention.
Figure 16:
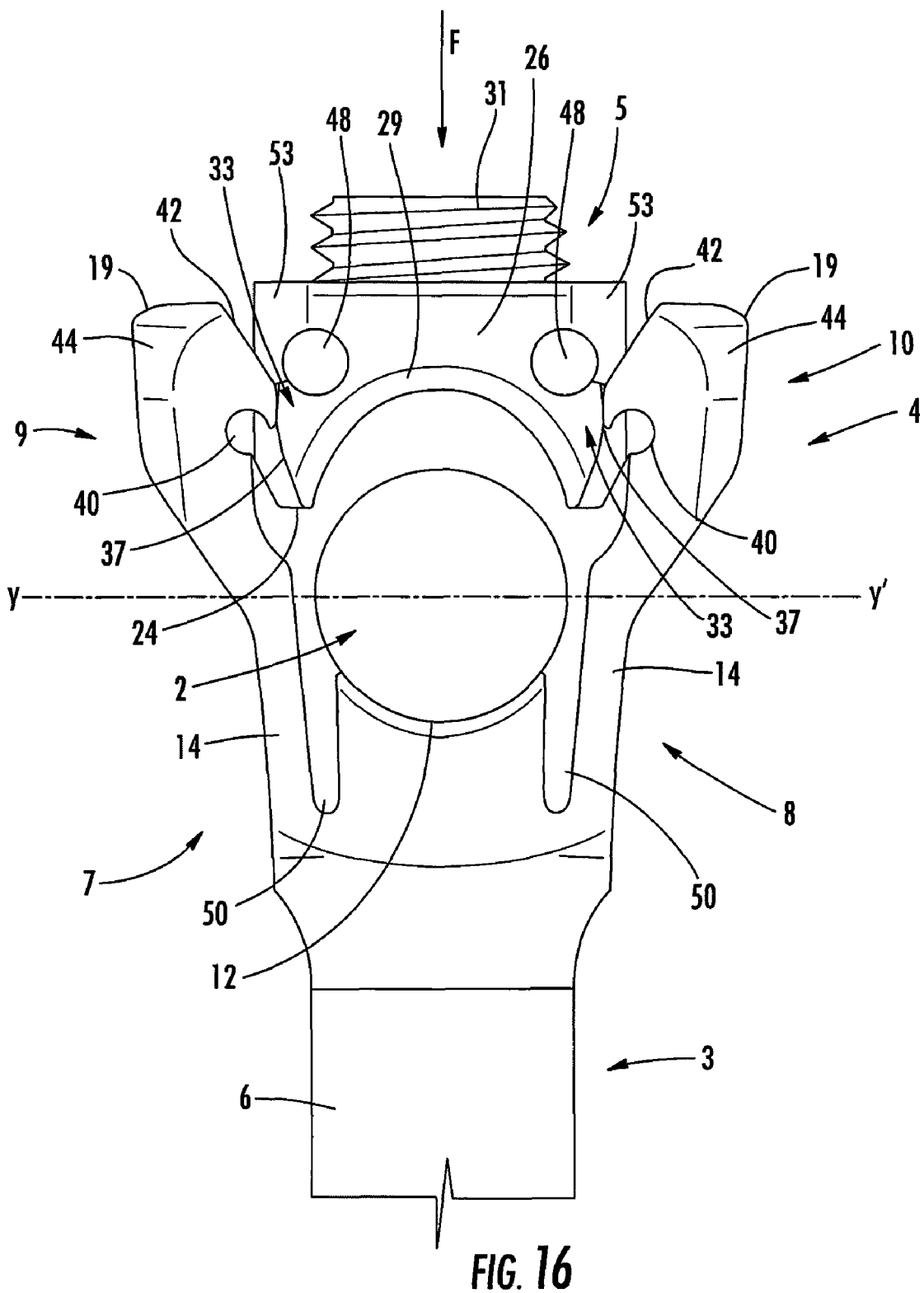
Figure 17:
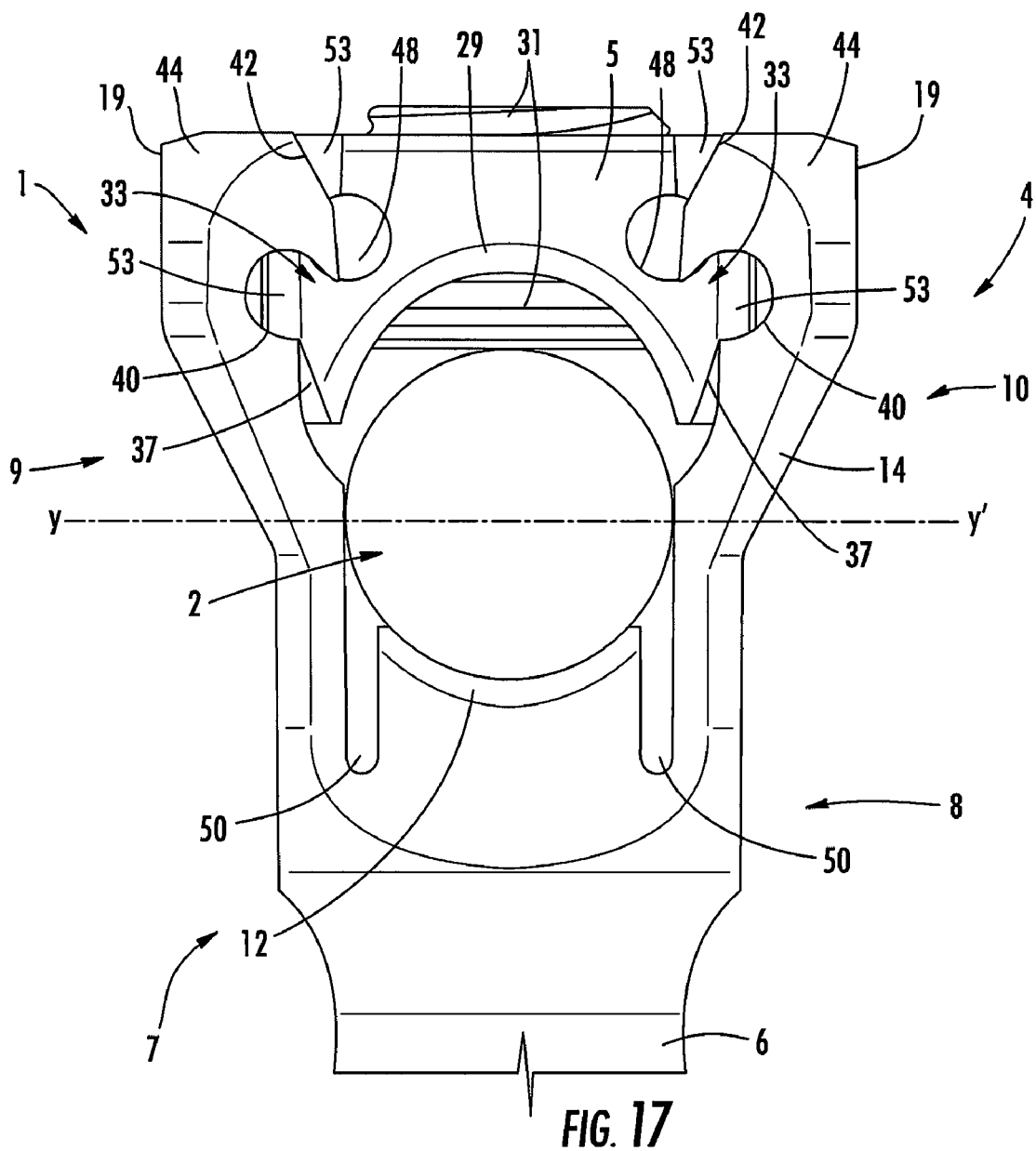
FIGS. 17 and 18 are perspective views showing a second modification of the immobilization device in the assembled position for blocking in rotation and translation the connecting rod of the rachidian implant.
Figure 18:
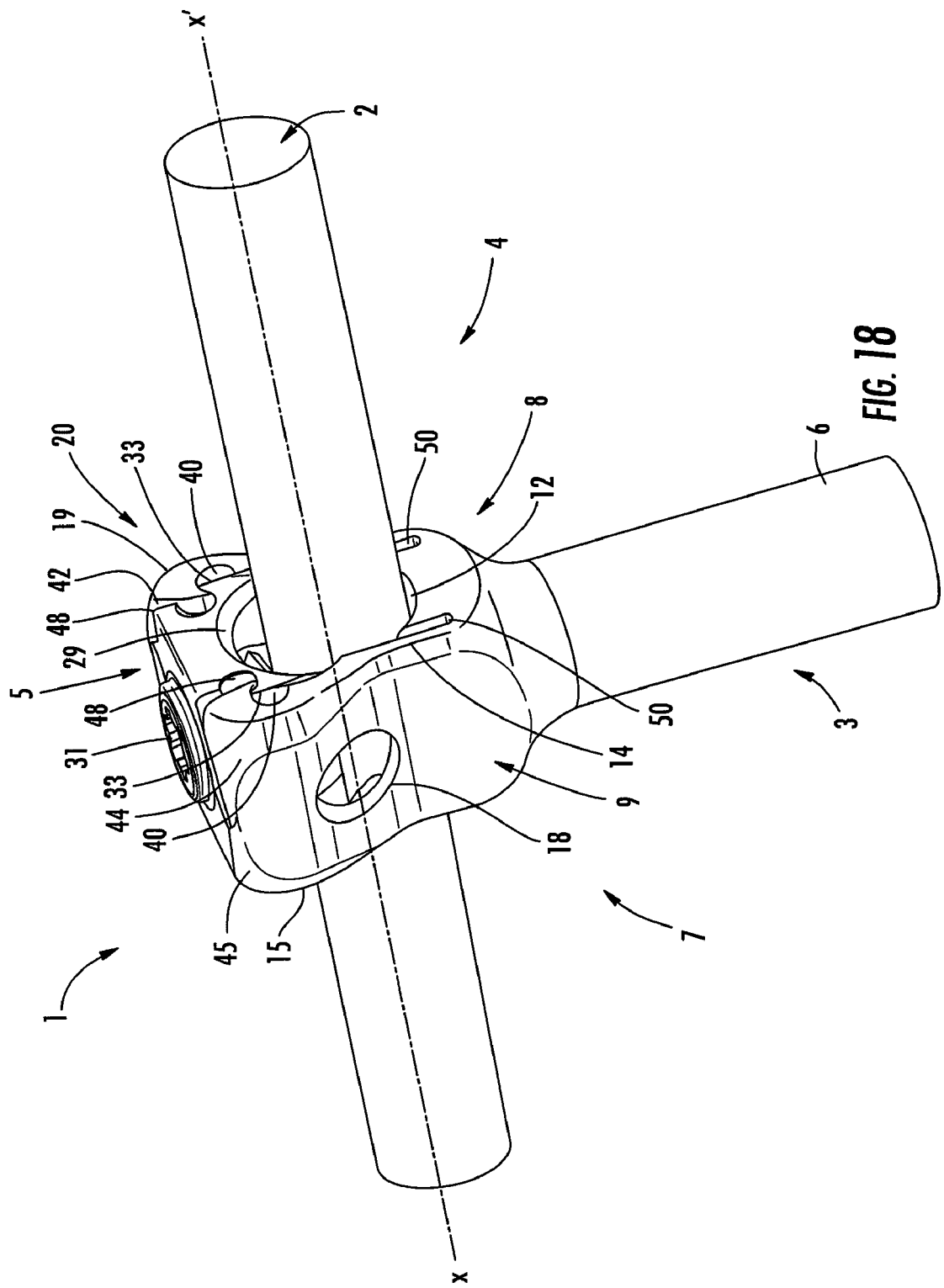

Each lug 33, 34 comprises respectively a hooking portion 48, 49 delimited by a cylindrical profile portion permitting coaction with the hooking portions 40, 41 of each tooth 19, 20 during emplacement of the blocking element 5 in the head 8 of the anchoring element 3 (FIG. 15).

Each lug 33, 34 has respectively an inclined external profile 37, 38 permitting sliding of said lugs and the elastic spacing of the walls 9, 10 and hence of the hooking blades 14, 15 in the direction YY' so as to be able to effect the assembly of the blocking element 5 with the osseous anchoring element 3.

It will be noted that each opposite surface 27, 28 comprises at its middle and between the lugs 33, 34 a vertical recess 52 bordered laterally by ribs 53 permitting the guidance of the blocking element 5 during its introduction into the head 8 of the anchoring element 3.

It will be seen that the hooking portions 48, 49 are closed opposite the lateral surfaces 25, 26 by means of the corresponding vertical rib 53 and disposed between each lugs 33, 34.

Each vertical rib 53 can have an external profile of any shape, provided that its profile will be complementary to that of the groove 54 provided in the thickness of the external surface of each vertical wall 9, 10 of the head 8 of the anchoring element 3.

The vertical seats 51 and 52 have a complementary part cylindrical profile so as to permit the introduction of an instrument so as to ensure the retraction of the blocking element 5 of the head 8 of the anchoring element 3.

There is shown in FIGS. 15 to 18 the different steps permitting the assembly of the blocking element 5 in the head 8 of the anchoring element 3 for the securement in rotation and in translation of the connecting rod 2 in each immobilization device 1 anchored in the vertebral body of a vertebra.

The connection rod 2 is positioned within the central opening 11 of the head 8 of the osseous anchoring element 3 before the introduction of the blocking element 5.

The emplacement of the blocking element 5 described above, in the head 8 of the anchoring element 3, is identical to that previously described in FIGS. 1 to 5.

The blocking element 5 is positioned above the head 8 of the osseous anchoring element 3 such that the lugs 33, 34 of a same lateral surface 27, 28 come to bear against the corresponding teeth 19, 20 of a same vertical wall 9, 10.

A pressure force F is generated in a substantially vertical direction with an instrument (not shown), on the blocking element 5, so that the lugs 33, 34 of each lateral surface 27, 28 deform laterally the vertical walls 9, 10 and hence the elastic hooking blades 14, 15.

The elastic deformation of the vertical walls 9, 10 takes place in the external direction of the head 8 because of the difference of dimensions provided between the lugs 33, 34 and the teeth 19, 20.

The introduction of the blocking element 5 is facilitated by the fact that each lug 33, 34 has a lower portion of inclined profile 37, 38 which slides on the external profile of each tooth 19, 20 of the hooking blades 14, 15 of each elastic wall 9, 10.

The pressure force F must be sufficient that each hooking portion 48, 49 of the lugs 33, 34 will come into snap fitting engagement with the hooking portion 40, 41 of each corresponding tooth 19, 20.

The retention of the blocking element 5 is achieved by the elasticity of the vertical walls 9, 10 and hence of the hooking blades 14, 15, which return to the rest position after the passage of the lugs 33, 34 over the corresponding teeth 19, 20.

The connecting rod 2 is adjusted by sliding in a cylindrical trough constituted by the part cylindrical bottom 12 of the head 8 of the osseous anchoring element 3 and the seat 29 having a part cylindrical profile of the blocking element 5.

The connecting rod 2 is then immobilized in rotation and in translation by means of the tightening screw 31 which is screwed into the bore 30 of the blocking element 5. The tightening screw 31, under the screwing force, blocks the connecting rod against the part cylindrical bottom 12 of the central opening 11 of the head 8 of the anchoring element 3.

Also, the screwing force of the pressure screw 31 against the connecting rod 2 permits, by means of vertical movement directed in a direction opposite that of said rod, to block the blocking element 5 in the head 8 of the anchoring element 3.

The retraction of the blocking element 5 is achieved by means of an instrument which is introduced into the vertical seats 51 and 52 so as to space apart the vertical walls 9, 10 in the outward direction of the head 8 of the anchoring element 3.

It must of course be understood that the preceding description is given only by way of example and that it in no way limits the scope of the invention from which one does not depart by replacing the details of execution described, by any other equivalent.

The invention claimed is:

1. An immobilization device, comprising: an osseous anchoring element provided with a head having two vertical walls delimiting a central U-shaped opening whose bottom has a part cylindrical profile, each vertical wall being separated from the bottom of the central opening by a vertical slot giving elasticity to each vertical wall, said vertical walls including respectively at each end a profile in the form of a hooking blade disposed facing each other and on opposite sides of the central opening, said hooking blades including respectively in their upper portion snap-in teeth, and a blocking element including a seat, a screw-threaded bore opening within the seat, a tightening screw coacting with the screw-threaded bore and lugs which coact respectively with said teeth, the blocking element having a lower surface including a seat having part cylindrical profile, and an upper surface including a screw-threaded bore opening within the seat and in which coacts a tightening screw, and lateral surfaces parallel two by two and of which at least two of the lateral surfaces are secured respectively to the lugs.

2. The immobilization device according to claim 1 wherein each vertical wall comprises on its internal surface and between the hooking blades a part cylindrical vertical seat having grooves on each side.

3. The immobilization device according to claim 1, wherein the teeth have a hooking profile turned inwardly of the central opening.

4. The immobilization device according to claim 3, wherein each of the teeth comprises above its hooking portion and in the direction of the opening an inclined external profile prolonged in the outward direction by a convexly rounded profile.

5. The immobilization device according to claim 1, wherein the lugs are in the form of teeth comprising hooking portions separated by a vertical seat bordered laterally by ribs.

6. The immobilization device according to claim 5, wherein the hooking portions are closed opposite the lateral surfaces by means of a corresponding one of the vertical ribs.

7. The immobilization device according to claim 1, wherein, each vertical wall includes a central surface bordered laterally and on each side by elastic blades separated respectively from said central surface by vertical slots.

8. The immobilization device according to claim 7, wherein the central surface of each vertical wall is pierced by a hole opening within the central U-shaped opening.

9. The immobilization device according to claim 7, wherein a second pair of the lateral surfaces are disposed in the width of said blocking element and positioned in prolongation of the first pair of lateral surfaces.

10. The immobilization device according to claim 7, wherein the pressure force applied to the blocking element permits by means of the lugs and the vertical slots a lateral deformation of the elastic blades in the direction of the central surface of each wall of the osseous anchoring element.

11. The immobilization device according to claim 1, wherein the teeth have an external profile which is convexly rounded and inclined.

12. The immobilization device according to claim 1, wherein a first pair of the lateral surfaces comprising respectively above the seat an impression adapted to coact with an instrument for the manipulation and emplacement of said blocking element on the osseous anchoring element.

13. The immobilization device according to claim 12, wherein each lug comprises respectively in its upper portion an inclined or beveled flat whose lower base is positioned in the plane containing each of said first pair of lateral surfaces.

14. The immobilization device according to claim 13, wherein each lug comprises respectively in its lower portion and opposite the inclined flats, a rounded profile.

15. The immobilization Immobilization device according to claim 1, wherein a distance separating two of the lugs is less than that provided between the teeth.

16. The immobilization device comprising: an osseous anchoring element provided with a head comprising two truncated vertical walls delimiting a central opening of U-shape whose bottom has a part cylindrical profile, each vertical wall being constituted by a central surface bordered laterally and on each side by elastic blades separated respectively from said central surface by vertical slots, said elastic blades including respectively in their upper portion a snap-in tooth and a blocking element comprising a seat with part cylindrical profile, a screw-threaded bore opening within said seat, a tightening screw coacting with the screw-threaded bore and lugs which coact respectively with teeth secured to the elastic blades, wherein the teeth have a hooking portion which is turned inwardly of the second opening and above the central surface of each vertical wall, and each of the teeth includes above its hooking portion and in the direction of the opening, an inclined external profile prolonged in the outward direction by a convexly curved profile.

17. The immobilization device according to claim 16, wherein a first central opening of U-shape carried by a first axis of the connecting rod and whose bottom has a part cylindrical profile, and a second opening perpendicular to the first axis and to the first opening.

18. The immobilization device according to claim 17 wherein the two perpendicular openings permit delimiting at each point of the elastic blades adapted to deform elastically under a pressure force.

19. The immobilization device according to claim 16 wherein the blocking element comprises at least four lateral surfaces parallel two by two and of which at least two are secured respectively to two lugs in the form of a tooth.

20. The immobilization device according to claim 19 wherein each lug comprises a hooking portion positioned retracted and spaced from the lateral surfaces and opposite two of the lateral surfaces of the blocking element.

* * * * *